United States Patent
Zhou et al.

(10) Patent No.: US 12,163,156 B2
(45) Date of Patent: Dec. 10, 2024

(54) CELL INDUCTION METHOD

(71) Applicant: INSTITUTE OF ZOOLOGY, CHINESE ACADEMY OF SCIENCES, Beijing (CN)

(72) Inventors: Qi Zhou, Beijing (CN); Wei Li, Beijing (CN); Zhengquan He, Beijing (CN); Liu Wang, Beijing (CN)

(73) Assignee: INSTITUTE OF ZOOLOGY, CHINESE ACADEMY OF SCIENCES, Beijing (CN)

( * ) Notice: Subject to any disclaimer, the term of this patent is extended or adjusted under 35 U.S.C. 154(b) by 1170 days.

(21) Appl. No.: 16/965,395

(22) PCT Filed: Jan. 29, 2019

(86) PCT No.: PCT/CN2019/073624
§ 371 (c)(1),
(2) Date: Jul. 28, 2020

(87) PCT Pub. No.: WO2019/144968
PCT Pub. Date: Aug. 1, 2019

(65) Prior Publication Data
US 2021/0230550 A1    Jul. 29, 2021

(30) Foreign Application Priority Data

| Jan. 29, 2018 | (CN) | ......................... | 201810083174.7 |
| Jan. 29, 2018 | (CN) | ......................... | 201810083568.2 |
| Jan. 29, 2018 | (CN) | ......................... | 201810083591.1 |

(51) Int. Cl.
*C12N 5/077* (2010.01)
*C12N 5/00* (2006.01)

(52) U.S. Cl.
CPC ......... *C12N 5/0653* (2013.01); *C12N 5/0018* (2013.01); *C12N 2501/155* (2013.01); *C12N 2506/1307* (2013.01)

(58) Field of Classification Search
CPC .................................................. C12N 5/067
See application file for complete search history.

(56) References Cited

U.S. PATENT DOCUMENTS

| 8,697,385 B1 | 4/2014 | Stefanovic |
| 9,279,106 B2 | 3/2016 | Schlegel et al. |
| 2013/0040302 A1 | 2/2013 | Burke et al. |
| 2013/0309681 A1* | 11/2013 | Schlegel ............ G01N 33/5091 435/6.12 |
| 2017/0065577 A1 | 3/2017 | Sander et al. |

FOREIGN PATENT DOCUMENTS

| CN | 102940631 | 2/2013 |
| CN | 104342401 | 2/2015 |
| CN | 104762324 | 7/2015 |
| CN | 105087476 | 11/2015 |
| CN | 105296418 | 2/2016 |
| CN | 105925524 | 9/2016 |
| CN | 106754636 | 5/2017 |
| CN | 107338214 | 11/2017 |
| JP | 2014-502151 | 1/2014 |
| WO | 2011/050476 | 5/2011 |
| WO | 2011/056416 | 5/2011 |
| WO | 2012/065067 | 5/2012 |

OTHER PUBLICATIONS

Doller et al. The cytoskeletal inhibitors latrunculin A and blebbistatin exert antitumorigenic properties in human hepatocellular carcinoma cells by interfering with intracellular HuR trafficking. Experimental Cell Research 2015, 330:66-80. (Year: 2015).*
International Search Report issued Apr. 28, 2019 in International (PCT) Application No. PCT/CN2019/073624.
Akihide Kamiya et al., "Stem and progenitor cell systems in liver development and regeneration", Hepatology Research, vol. 45, 2015, pp. 29-37.
Partial Supplementary European Search Report issued Sep. 15, 2021 in corresponding European Patent Application No. 19744381. 5, 16 pages.
Martens et al., "Softening of the actin cytoskeleton by inhibition of myosin II", Eur J Physiol, Cell and Molecular Physiology, 2008, vol. 456, pp. 95-100.
Wang et al., "The Progress of Study of Immortalized Skin Fibroblasts", Journal of Chinese Biotechnology, 2002, vol. 22, No. 4, pp. 62-65.
Takeda et al., "Direct conversion of human fibroblasts to brown adipocytes by small chemical compounds", Scientific Reports, 2017, vol. 7, No. 1, pp. 1-11.

(Continued)

*Primary Examiner* — Allison M Fox
*Assistant Examiner* — Jennifer S Spence
(74) *Attorney, Agent, or Firm* — Wenderoth, Lind & Ponack, L.L.P.

(57) ABSTRACT

The present invention relates to a cell induction method, in particular to a method for inducing differentiation of fibroblasts into adipocytes, comprising the following steps: Cultivating the fibroblasts in a culture medium, adding a Myosin inhibitor and BMP4 to the culture medium, and continuously cultivating same until adipocytes are obtained. The present invention further relates to a method for inducing the conversion of fibroblasts into immortalized cells and use thereof. The method comprises the following steps: cultivating the fibroblasts in a culture medium, adding Myosin inhibitor to the culture medium, and continuously cultivating same until immortalized cells are obtained. The present invention further relates to a method for inducing in vitro amplification of hepatocytes. The present invention further relates to use of a Myosin inhibitor, especially (−)-Blebbistatin or (S)-(−)-Blebbistatin, O-Benzoate, and hepatocytes obtained by means of the method for inducing in vitro amplification of hepatocytes, constructing of bioartificial livers, and constructing models of liver disease.

3 Claims, 11 Drawing Sheets

(56) References Cited

OTHER PUBLICATIONS

Kuan-Liang et al., "Inhibition of Rock-Myosin II Signaling Pathway Enables Culturing of Human Pluripotent Stem Cells on Microcarriers Without Extracellular Matrix Coating", Tissue Engineering, Part C, 2014, vol. 20, No. 3, pp. 227-238.
Jana Vukovic et al., "A Novel Fluorescent Reporter CDy 1 Enriches for Neural Stem Cells Derived from the Murine Brain" Stem Cells and Development, vol. 22, No. 15 (Mar. 21, 2013) pp. 2341-2345 (6 pages).
Mito Kanatsu-Shinohara et al., "Enrichment of Mouse Spermatogonial Stem Cells by the Stem Cell Dye CDy1[1]", Biology of Reproduction, vol. 94, No. 1, Article 13 (Nov. 25, 2015) pp. 1-10 (10 pages).

\* cited by examiner

Passage with enzymatic digestion, P3

Passage with enzymatic digestion, P5

CELL INDUCTION METHOD

TECHNICAL FIELD

The present invention relates to the field of biotechnology, particularly to the field of cell induction technology, and more particularly to a method for inducing transdifferentiation of fibroblasts into adipocytes and use thereof, a method for transforming fibroblasts into immortalized cells and use thereof, and a method for inducing in vitro amplification of hepatocytes.

BACKGROUND ART

Transdifferentiation (also known as transformation of differentiation) refers to the phenomenon of one type of differentiated cells transforming into another type of differentiated cells. At present, multiple types of cell have been transdifferentiated, for example, the transdifferentiation of embryonic fibroblasts, chondroblasts and retinal epithelial cells into myocytes; B-lymphocytes into macrophages; and mouse fibroblasts into functional nerve cells, and the like.

Adipocytes are abundant in adults. The tissue of adipocytes is also called adipose tissue and is often white. Adipocytes proliferate in a large number in early childhood and reach a peak in puberty, after that the number of them generally does not increase. In the body of normal animals and humans, adipose tissue mainly exists in the enterocoelia and the subcutaneous tissue of the abdomen, but adipose tissue exists in various parts of the body of obese patients, for example, around the organs including kidney, mesentery, subcutaneous tissue, and enterocoelia, indicating that not only preadipocytes may differentiate into adipocytes, but also some non-preadipocytes may differentiate into adipocytes under some specific conditions, this subverts the traditional view that adipocytes are differentiated from preadipocytes. By transdifferentiation of non-preadipocytes into adipocytes, the transformation mechanism of adipocytes can be more clearly understood, which in turn guides the development of anti-obesity drugs.

Fibroblasts are the main cellular component of loose connective tissue, and are differentiated from mesenchymal cells during embryonic period. Transdifferentiation of fibroblasts into adipocytes has important application in many fields. For example, transdifferentiation of the most common type of myofibroblasts found in wound scar into adipocytes may achieve wound healing without any scar in the future; in addition, the regeneration of adipocytes in wrinkled skin is possible to derive a new anti-aging treatment strategy. Thus, it is important to realize the transdifferentiation of non-preadipocytes, especially fibroblasts, into adipocytes.

Currently, the prior art has disclosed some methods for inducing transdifferentiation of fibroblasts into adipocytes. CN104342401B discloses a method for promoting the transdifferentiation of fibroblasts into adipocytes by using a defined combination of cytokines, and the effective factors of such a composition are epidermal growth factor, hepatocyte growth factor, dexamethasone, insulin and PPARγ agonist. CN104372024A discloses a method for inducing transdifferentiation of bovine fibroblasts/myoblasts into adipocytes, comprising cloning a bovine transcription factor CCAAT enhancer binding protein C/EBPβ gene, constructing a C/EBPβ gene overexpression vector and packaging to obtain a recombinant adenovirus, infecting bovine fibroblasts and myoblasts with the adenovirus to achieve rapid transdifferentiation of these cells into adipocytes. Since the above method uses a large number of macromolecular substances or reprogramming process, the efficiency is low, and the safety is also affected in some degree.

It has been demonstrated that small molecule compounds may also induce transdifferentiation of fibroblasts into adipocytes, and this increases the speed, survival and ability of the transdifferentiation. For example, CN105754935A discloses an induction medium for inducing transdifferentiation of fibroblasts into adipocytes, the medium comprises a basal medium and a small molecule combination for induction, and the small molecule combination for induction is SG or 6TF, wherein S represents SB431542, G represents GSK126, 6 represents E61541, T represents tranylcypromine, and F represents forskolin. However, there is still a need to explore more small molecule compounds for inducing transdifferentiation of fibroblasts into adipocytes for disease research, treatment, and broader applications.

Normal tissue-derived somatic cells may grow and divide under normal in vitro culture conditions, but after a limited number of cell passages, the proliferation will be ceased, then senescence and death occur, this limits the application of cell culture techniques. Cell immortalization means that in the process of in vitro culture, cells escape from the crisis of proliferative aging due to their own genetic changes or various external stimuli, thereby avoiding the aging and death process of normal cells, thus the immortalized cells can be subcultured for a long time, divide and proliferate unlimitedly.

A large number of studies have been carried out on the mechanisms and methods of cell immortalization. It has been confirmed that radioactive factors, telomerase activation, viral gene transfection, protooncogenes and tumor suppressor genes can lead to infinite proliferation and division of cells. But after years of research it is found that, although there are resemblances among the mechanisms of immortalization, the same immortalization method is not applicable to all cells. For example, the methods for immortalization of hepatocytes include tumor suppressor gene knockout, plasmid transduction and viral transfection, reversible immortalization, etc. The methods for immortalization of epithelial cells include DNA oncogenic virus transfection, etc. As to the methods for immortalization of cardiomyocytes, there are successful cases of P16 lentiviral vector and reversible SV40 viral transduction pathway.

At present, the prior art has disclosed some methods for inducing transformation of fibroblasts into immortalized cells. Wang Xinwen et al. ("The Progress of Study of Immortalized Skin Fibroblasts", *China Biotechnology*, Vol. 22, No. 4, August 2002) disclosed methods for immortalization of skin fibroblasts. In addition to the above commonly used methods, in summary, there are several methods: HPV, tetranitroquinoline monooxide, aflatoxin, and the like.

Targeted development of immortalization technology for specific cells can achieve long-term passage, infinite division and proliferation, and increased cell cycle life of normal somatic cells with less passages and slower proliferation and division. This not only helps to understand the rule of cell growth, explores the causes of cell aging, but also has important clinical significance for solving the problem of organ transplantation.

In addition, the data shows that cell immortalization is the premise of transformation into tumor cells, and it is a necessary stage for transformation of normal cells into tumor cells. Studying the immortalization of cells can lay a solid foundation for treating tumors and controlling the proliferation of tumor cells.

Therefore, researches on transformation of fibroblasts into immortalized cells have broad application prospects.

The liver is the largest internal organ in the human body, and is the main site of metabolism. Hepatocytes account for 85% of the liver. Hepatocytes have strong regenerative potential in vivo, if two third of the normal liver is resected, and then it can restore to its original volume by cell proliferation in just one week. However, unfortunately, although human liver can be rapidly regenerated in vivo, under in vitro cultural conditions the primary hepatocytes can only proliferate in a short period of time and cannot proliferate over time. So far, efforts to amplify human hepatocytes in the laboratory have led to immortalized cancer cells with low metabolic functions. The scarcity of human hepatocytes and the loss of function during hepatocyte amplification are the main bottlenecks in the development of science, medicine and pharmacy. Solving this problem will help to promote researches and applications such as the in vitro drug metabolism of hepatocytes, drug toxicity, end-stage liver disease cell therapy, construction of artificial liver to support patients waiting for transplantation, and construction of disease model.

Currently, the most commonly used method in this field is the transcription factor reprogramming technique, but such techniques have a greater risk of entering clinical applications due to the insertion of foreign gene fragments. Previous studies have found that with the small molecule reprogramming technology, each of the two research teams in China and Japan successfully realized transformation and rapid proliferation of primary hepatocytes into hepatic precursor cells in vitro; after directive induction of differentiation, the proliferated precursor-like hepatocytes can regain the function of mature hepatocytes, and more than 70% of the integration can be reached after transplantation into the mice. With small molecule compound reprogramming technology, the resulting hepatocytes have not undergone any genetic engineering, and thus they are closer to the initial state of the cells in the body, and are safer and more effective for future clinical applications. There is still a strong need in the art to use small molecule compounds to induce in vitro amplification of hepatocytes.

Contents of the Invention

The inventors have continually explored and unexpectedly found that, the above object can be achieved by using Myosin inhibitor (−)-Blebbistatin or (S)-(−)-Blebbistatin O-Benzoate.

Thus, the present invention relates to use of a Myosin inhibitor in induction of cell transdifferentiation.

Preferably, the transdifferentiation is to induce fibroblast transdifferentiation. Preferably, the transdifferentiation is to induce transdifferentiation of fibroblasts into adipocytes.

In one embodiment, the Myosin inhibitor is (−)-Blebbistatin (abbreviated as Ble, or Bleb, or Blebb).

In one embodiment, the Myosin inhibitor is (−)-Blebbistatin O-Benzoate (abbreviated as S-Bleb-OB).

The (−)-Blebbistatin (also referred to as (S)-(−)-Blebbistatin, or S-Bleb) used in the present invention is a cell permeable inhibitor acting on non-Myosin II ATPase, it does not inhibit myosin light chain kinase, while inhibits the constriction of cleavage furrows and does not interfere with mitosis or the assembly of contractile rings. Its structural formula is as shown in formula (I) with a molecular weight of 292.33.

The (−)-Blebbistatin O-Benzoate (also referred to as (S)-(−)-Blebbistatin O-Benzoate, or S-Bleb-OB) used in the present invention is a derivative of (−)-Blebbistatin, and its structural formula is as follows.

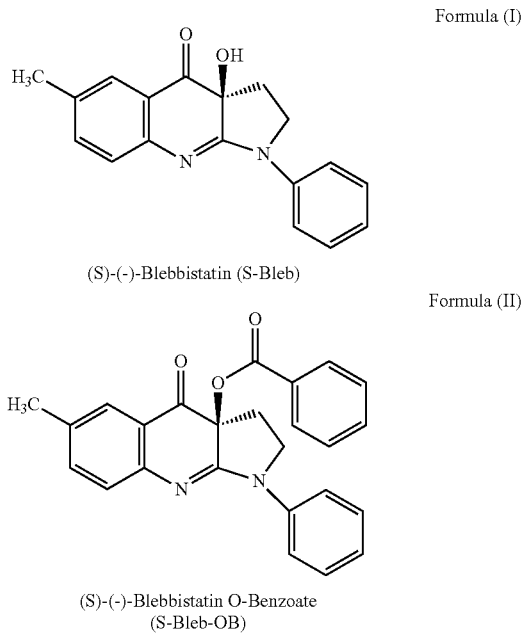

Formula (I)

(S)-(−)-Blebbistatin (S-Bleb)

Formula (II)

(S)-(−)-Blebbistatin O-Benzoate (S-Bleb-OB)

The present invention also relates to a method for inducing transdifferentiation of fibroblasts into adipocytes, comprising the steps of: culturing fibroblasts in a medium, adding a Myosin inhibitor and BMP4 to the medium, and continuously culturing the cells until adipocytes are obtained.

Preferably, the medium comprises any one or more of a basal medium, fetal calf serum, and an adipocyte induction medium.

Preferably, the basal medium comprises high glucose DMEM, fetal calf serum and double antibiotics.

Preferably, the adipocyte induction medium comprises N2B27 medium (1:1 mixture of DMEM/F12 and Neurobasal), N2 additive, B27 additive, 2% bovine serum albumin, β-mercaptoethanol, GlutaMAX, which is an L-alanyl-L-glutamine dipeptide, insulin and double antibiotics, and serum substitutes. The B27 additive is a commercial serum-free cell culture additive containing Biotin, Selenium, L-carnitine, T3 (triodo-1-thyronine), Corticosterone, DL-α-tocopherol (vitamin E), Ethanolamine, DL-α-tocopherol acetate, D(+)-galactose, Glutathione (reduced), Linoleic acid, Linolenic acid, Progesterone, Putrescine, Retinyl acetate, and Proteins (Albumin, bovine: Catalase: Insulin: Superoxide dismutase: Transferrin).

The present invention also relates to adipocytes obtained by the method described, or a reagent, or a research tool, or a diagnostic tool comprising the adipocytes.

The above mentioned method of the present invention only needs the treatment of a single small molecule or a single factor, and has simple operation, good repeatability; it can be efficiently performed in vitro and in vivo without involving transgenic operation, and has good safety of the obtained adipocytes, and it is applicable to tissue regeneration, repair, and other fields and industries.

The present invention also relates to use of a myosin inhibitor in the induction of cell immortalization.

Preferably, the immortalization is to induce transformation of fibroblasts into immortalized cells.

Preferably, the Myosin inhibitor is (−)-Blebbistatin, or (S)-(−)-Blebbistatin O-Benzoate.

The present invention also relates to a method for inducing transformation of fibroblasts into immortalized cells, comprising the steps of: culturing fibroblasts in a medium, adding a Myosin inhibitor to the medium, and continuously culturing the cells until immortalized cells are obtained.

Preferably, the medium comprises any one or more of a basal medium, fetal calf serum, and an immortalization-inducing medium.

The present invention also relates to a medium for inducing transformation of fibroblasts into immortalized cells, which is characterized in that it comprises a Myosin inhibitor, a basal medium, fetal calf serum and an immortalization-inducing medium.

Preferably, the basal medium comprises high glucose DMEM and double antibiotics, and/or the immortalization-inducing medium comprises N2B27 medium (1:1 mixture of DMEM/F12 and Neurobasal), N2 additive, B27 additive, 2% bovine serum albumin, β-mercaptoethanol, GlutaMAX, insulin, and double antibiotics.

Preferably, the immortalization-inducing medium further comprises one or more of KOSR, CHIR99021 and A83-01.

The present invention also relates to immortalized cells obtained by the method described above, or a reagent or a research tool or a diagnostic tool comprising the immortalized cells.

The present invention also relates to use of a gene in the preparation of a preparation for inducing proliferation or aging, which is characterized in that the gene comprises one or more of Sox2, Srrt, Yap, β-catenin, Mki67, Pcna, P19, P16ink4a, P15ink4b, Morf41, and Elf5.

Preferably, the proliferation-related gene comprises one or more of Sox2, Srrt, Yap, $-catenin, Mki67, and Pcna. Preferably, the aging-related gene comprises one or more of P19, P16ink4a, P15ink4b, Morf41, and Elf5.

The above mentioned method of the present invention only needs the treatment of a single small molecule or a single factor, and has simple operation, good repeatability; it can be efficiently performed in vitro and in vivo without involving transgenic operation, and has good safety of the obtained immortalized cells, and it is suitable for understanding the rule of cell growth, exploring the causes of cell aging, and solving the problem of organ transplantation; it can also lay a foundation for the treatment of tumors and controlling the proliferation of tumor cells, and is of great significance. The present invention also finds proliferation-related genes and aging-related genes, and provides a novel alternative for inducing cell proliferation and senescence.

Further, the inventors have continually explored and unexpectedly found that the Myosin inhibitor can significantly promote long-term amplification of hepatocytes, thereby achieving the above object.

Thus, the present invention generally relates to use of a Myosin inhibitor in the induction of in vitro amplification of hepatocytes.

The present invention also relates to use of a Myosin inhibitor in the construction of a bioartificial liver.

The present invention also relates to use of a Myosin inhibitor in the construction of a liver disease model.

Preferably, the Myosin inhibitor is (−)-Blebbistatin, or (S)-(−)-Blebbistatin O-Benzoate.

The present invention also relates to a method for inducing in vitro amplification of hepatocytes, which is characterized in that it comprises the steps of: culturing hepatocytes in a medium, adding a Myosin inhibitor to the medium, and continuously culturing the cells to induce in vitro amplification of hepatocytes. Preferably, the Myosin inhibitor is (−)-Blebbistatin, or (S)-(−)-Blebbistatin O-Benzoate.

The present invention also relates to hepatocytes obtained by the method.

The present invention also relates to a reagent, a bioartificial liver, a research tool, or a diagnostic tool comprising the hepatocytes.

The present invention also relates to a liver disease model using the method for inducing in vitro amplification of hepatocytes, or using the hepatocytes obtained by said method.

The present invention also relates to use of hepatocytes obtained by the method in the construction of a bioartificial liver.

The present invention also relates to use of hepatocytes obtained by the method in the construction of a liver disease model.

The uses described above may be therapeutic or non-therapeutic.

The methods according to the present invention only needs the treatment of a single small molecule or a single factor, and has simple operation, good repeatability; it can be efficiently performed in vitro without involving transcription factor reprogramming technology and complex transgenic operation, and conduct amplification for a long time. In addition, the hepatocytes amplified with small molecules are still functional.

SPECIFIC EMBODIMENTS

Figure 1:
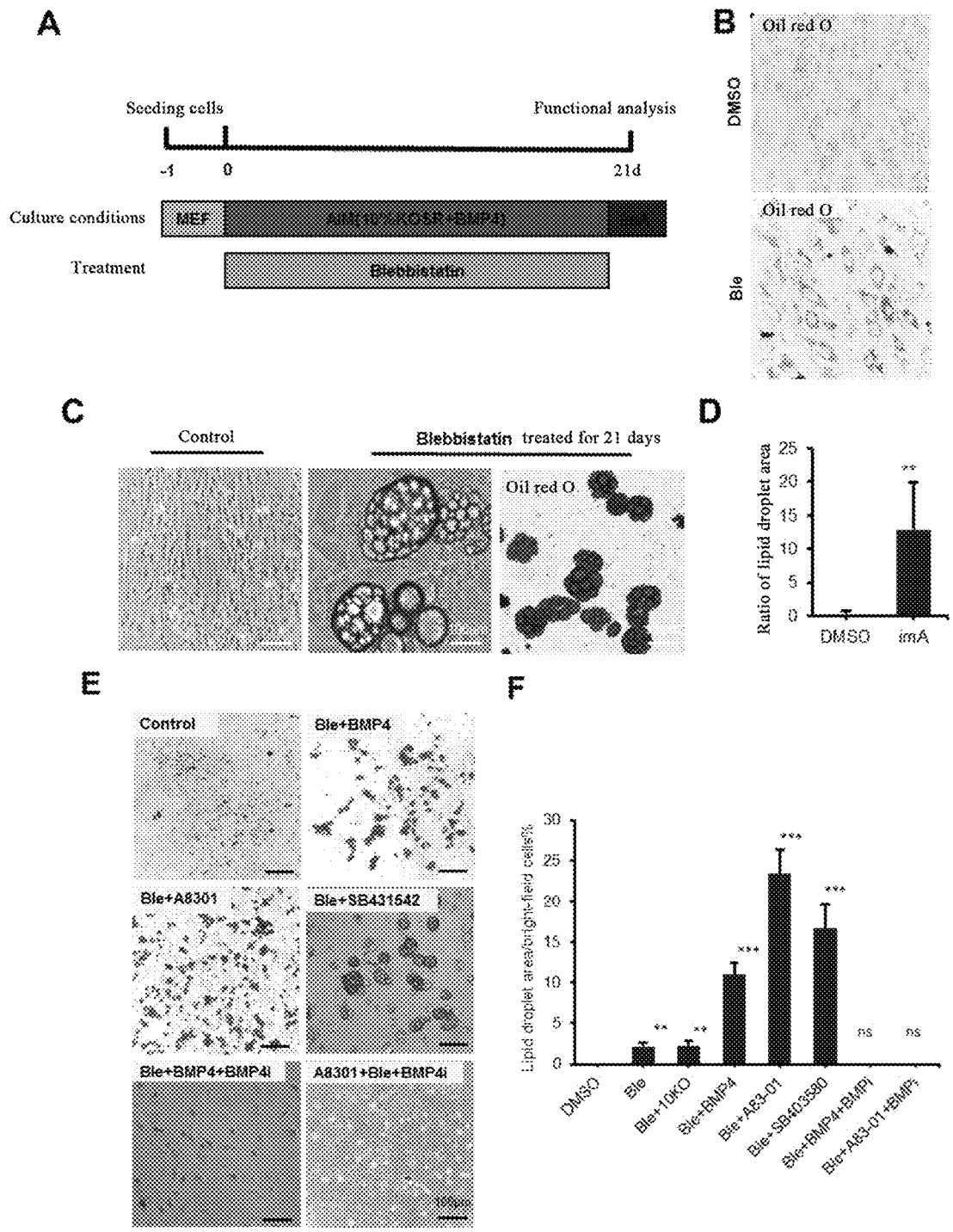
FIG. 1A is an experimental flow of Example 1.
FIG. 1B shows the oil red O staining of adipocytes induced from human foreskin fibroblasts.
FIG. 1C and FIG. 1D show the morphology, the oil red O staining, and the area ratio of lipid droplets of adipocytes obtained from mouse embryonic fibroblasts, respectively.
FIG. 1E and FIG. 1F show the oil red O staining and lipid droplet area statistics respectively, after addition of different substances in the original adipocyte induction medium.

Specific examples of the present invention will be described in more detail below with reference to the accompanying drawings. Although the specific examples of the present invention are shown in the accompanying drawings, it should be understood that the present invention may be implemented in various ways and not be limited by the examples described herein. On the contrary, these examples are provided so that this invention may be more fully understood, and the scope of the present invention can be fully conveyed to those skilled in the art.

It should be noted that certain words are used in the specification and claims to refer to specific components. Those skilled in the art will appreciate that a skilled person may refer to the same component by different nouns. The present specification and claims do not use the difference of nouns as a means of distinguishing components, but rather use the functional differences as a criterion for distinguishing components. The word "comprise/comprising" or "include/including" as used throughout the specification and claims is an open term, and should be interpreted as "including but not limited to". The following description of the specification is the preferred embodiments for implementing the present invention, however, it is for the purpose of the general principles of the specification, and is not intended to limit the scope of the present invention. The scope of the present invention is defined by the appended claims.

As used herein, "substantially free" with respect to a specific component means that a specific component has not been purposefully formulated into a composition, and/or it is present only as a contaminant or in trace amount. Thus, the total amount of a specific component resulting from any accidental contamination of the composition is less than 0.05%, preferably less than 0.01%. Most preferred compositions are those in which the amount of such a specific component is not detectable by standard analytical methods.

As used herein, "a" or "an" can mean one or more. As used in the claims, when used in conjunction with the word "comprise/comprising", the word "a" or "an" can mean one or more than one.

The word "or" is used in the claims to mean "and/or", unless it is specifically indicated that it only refers to an alternative, or the alternatives are mutually exclusive, although the disclosure supports referring to just an alternative and the definition of "and/or". As used herein, "another" can mean at least a second or more.

Throughout this application, the term "about" is used to indicate that the value includes an inherent change in the error of a device, a change in the method for determining the value, or a change existing between research objects.

In this context, "differentiation" means a process of changing less specialized cells into more specialized cell types. "Dedifferentiation" is a cellular process in which a partially or terminally differentiated cell returns to an earlier stage of development, such as pluripotency or multipotency. "Transdifferentiation" is a process of transforming one differentiated cell type into another. Typically, transdifferentiation occurs by programming and the cells do not undergo an intermediate pluripotency stage, i.e., the cells are programmed directly from one differentiated cell type to another differentiated cell type.

As used herein, the term "subject" or "subject in need" refers to a mammal, preferably a human, of a male or female at any age, which requires cell or tissue transplantation. Typically, a subject requires cell or tissue transplantation (also referred to herein as a receptor) due to a disorder or pathology, or an undesired condition, status or syndrome, or an abnormity of body, morphology or physiology suitable for treatment via cell or tissue transplantation.

Some of the terms used herein are defined as follows:

BMP4: bone morphogenetic protein 4 (bmp4).

High glucose DMEM: a high glucose DMEM medium (dulbecco's modified eagle medium, DMEM), i.e., a commercial medium containing various glucoses and amino acids, which is developed on the basis of MEM medium.

N2B27: a well-defined cell culture medium containing a 1:1 mixture of DMEM/F12 basal medium and Neurobasal basal medium, N2 additive and B27 additive; it is reported in favor of differentiation of mouse embryonic stem cells into nerve direction.

DMEM/F12: a commercial basal medium containing a 1:1 mixture of DMEM medium and F12 medium, suitable for clonal density culture.

Neurobasal: a commercial basal medium that is in favor of the culture of nerve cells.

GlutaMAX: a cell culture additive that can directly replaces L-glutamine in a cell culture medium.

Double antibiotics: penicillin and streptomycin are two commonly used antibiotics in cell culture to prevent bacterial contamination during cell culture.

N2 additive: a commercial serum-free cell culture additive.

B27 additive: a commercial serum-free cell culture additive.

KOSR: a commercial knockout serum replacement (KOSR).

CHIR99021: a GSK-3α/β inhibitor commonly used as an activator of the Wnt signaling pathway.

A83-01: a selective TGF-β inhibitor that significantly inhibits the activity of ALK4, ALK5 and ALK7.

EXAMPLES

The embodiments of the present invention are exemplified and described in detail below by way of specific examples. However, the following contents should not be construed as limiting the present invention in any way. The materials and the like used in the examples are all commercially available unless otherwise specified.

Example 1: Transformation of Fibroblasts to Adipocytes

Taking a 12-well plate as an example (coming, 3335), for each well, preparing 20 µg/ml Matrigel solution (BD, 354277) with 1×DMEM and coating for 12 hours; then the coating solution is removed, washing with 1×PBS.

Mouse embryonic fibroblasts (C57, prepared by E13.5) or adult foreskin fibroblasts (HFF20y, Beijing Stem Cell Bank) are uniformly seeded in each well, 1×10$^4$ cells per well; incubating in basic medium (high glucose DMEM (Gibco, C12430500BT), double antibiotics) added with 10% fetal bovine serum (Gibco, 16000-044) for 24 hours. The medium is removed, then washing with PBS.

The fibroblasts treated as described above are added to an adipocyte induction medium: (N2B27 medium: 1:1 mixture of DMEM/F12 (Gibco, 10565018) and Neurobasal (Gibco, 21103-049), added with N2 additive (100×, Gibco, 17502084), B27 additive (50×, Gibco, 17504044), 2% bovine serum albumin (1000×, sigma, A8022), β-mercaptoethanol (1000×, Gibco, 21985023), GlutaMAX (200×, Gibco, 35050-061), 1 μg/ml insulin (Roche, 11376497001), double antibiotics); 10% serum substitute (Gibco, 10828-028) added with Myosin inhibitor (100 mM concentrated stock of dimethyl sulfoxide solution (sigma, D2650), storing at −20° C. in the dark for 1 month) and 10 ng/ml BMP4 (Peprotech, 10828-028), and identifying after 21 days of cultivation, the experimental flow is shown in FIG. 1A.

The identification of adipocytes is performed by oil red staining of cells, oil red O staining solution (cell-specific, Solarbio, G1262) is used, and the details are as follows: removing the medium, adding ORO Fixative to fix for 10-15 min, removing the ORO Fixative, and placing in flowing air for 10-15 min. At this time, ORO Stain is prepared in a ratio of ORO Stain A:ORO Stain B=3:2, standing for 10 min after mixing, then adding to the well; the staining solution is removed after dip dyeing for 15 min, adding 60% isopropanol to rinse for 20-30 s, and washing with distilled water for 3 times, then taking photos under an optical microscope. The neutral fats are orange-red or orange-colored, and the phospholipids are pink. The red oil O staining of adipocytes induced by human foreskin fibroblasts is shown in FIG. 1B.

The morphology of adipocytes obtained from mouse embryonic fibroblasts and the oil red O staining thereof are shown in FIG. 1C, and the formation of orange-red lipid droplets is observed, indicating the appearance of neutral fats. The area ratio of lipid droplets is nearly 13%, which is significantly higher than that of the control group ($P<0.01$). The statistical results are shown in FIG. 1D.

Addition of 10 μM A83-01 (stemgent, 04-0014) to the original adipocyte induction medium significantly increases the adipocyte induction efficiency by up to 20% ($P<0.001$); or addition of 10 μM SB431542 (stemgent, 04-0010-10) also significant increases the adipocyte induction efficiency by 18% ($P<0.001$). If an inhibitor of BMP is added, the adipocyte induction efficiency is restored to the control level. Oil red O staining is shown in FIG. 1E, and the statistics of lipid droplet area is shown in FIG. 1F.

Figure 2:
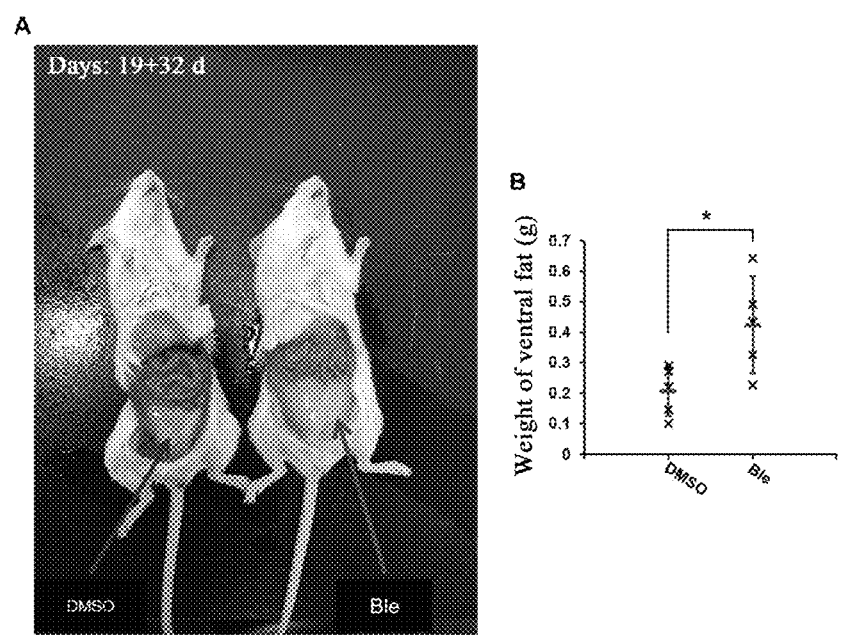
FIGS. 2A and 2B show in vivo experimental results of small molecule treatments, indicating significant increase in ventral fat content. Ble in the figures represents (−)-Blebbistatin.

In vivo experiment: the same batch of 6-8 week-old ICR female mice are selected and randomly divided into two groups, 5 in each group. As to one group, small molecule (−)-Blebbistatin or (S)-(−)-Blebbistatin O-Benzoate (0.5 mg/kg, dissolved in 10% DMSO+2% Tween 80+normal saline) is injected into the ventral side of the mice; as to the other group, the same amount of DMSO as the small molecule group is injected in the same way as the experimental group. The injection is performed once a day, 19 days after the injection, and the drug is stopped for 32 days. The mice are sacrificed by cervical dislocation, and the ventral fat content is observed. The results are shown in FIG. 2, and the small molecule treatment group can significantly increase the ventral fat content, as shown in FIGS. 2A and 2B. In addition, treating with (S)-(−)-Blebbistatin O-Benzoate instead of (−)-Blebbistatin also increases ventral fat content, and the experimental results show that without optimization, the ventral fat content increases by about 50%.

Example 2: Transformation of Fibroblasts to Immortalized Cells

Taking a 12-well plate as an example (coming, 3335), for each well, preparing 20 μg/ml Matrigel solution (BD, 354277) with 1×DMEM and coating for 12 hours; then the coating solution is removed, washing with 1×PBS.

Mouse embryonic fibroblasts (C57, prepared by E13.5) or tail-tip fibroblasts (prepared from one week-old mice or adult mice) are uniformly seeded in each well, 2×10$^4$ cells per well; incubating in basal medium (high glucose DMEM (Gibco, C12430500BT), double antibiotics) added with 10% fetal bovine serum (Gibco, 16000-044) for 24 hours. The medium is removed, then washing with PBS.

Figure 3:
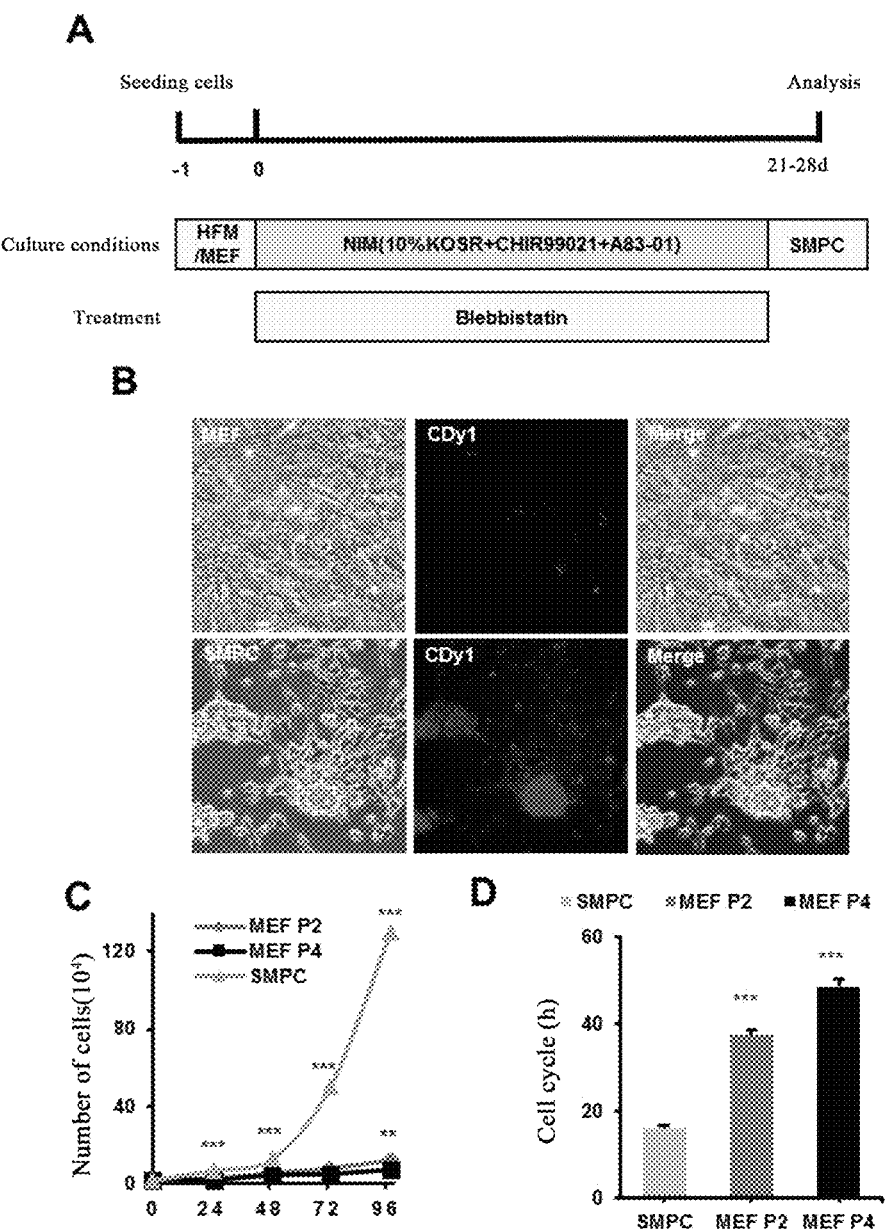
FIG. 3A is an experimental flow of Example 2.
FIG. 3B shows the results of observation by fluorescence microscopy.
FIGS. 3C and 3D show the plotted cell growth curves and calculated cell cycles.
FIGS. 3E and 3F show the results of composition analysis of cell cycle.
FIGS. 3G and 3H show the detection results of proliferation and senescence genes.
Figure 3:
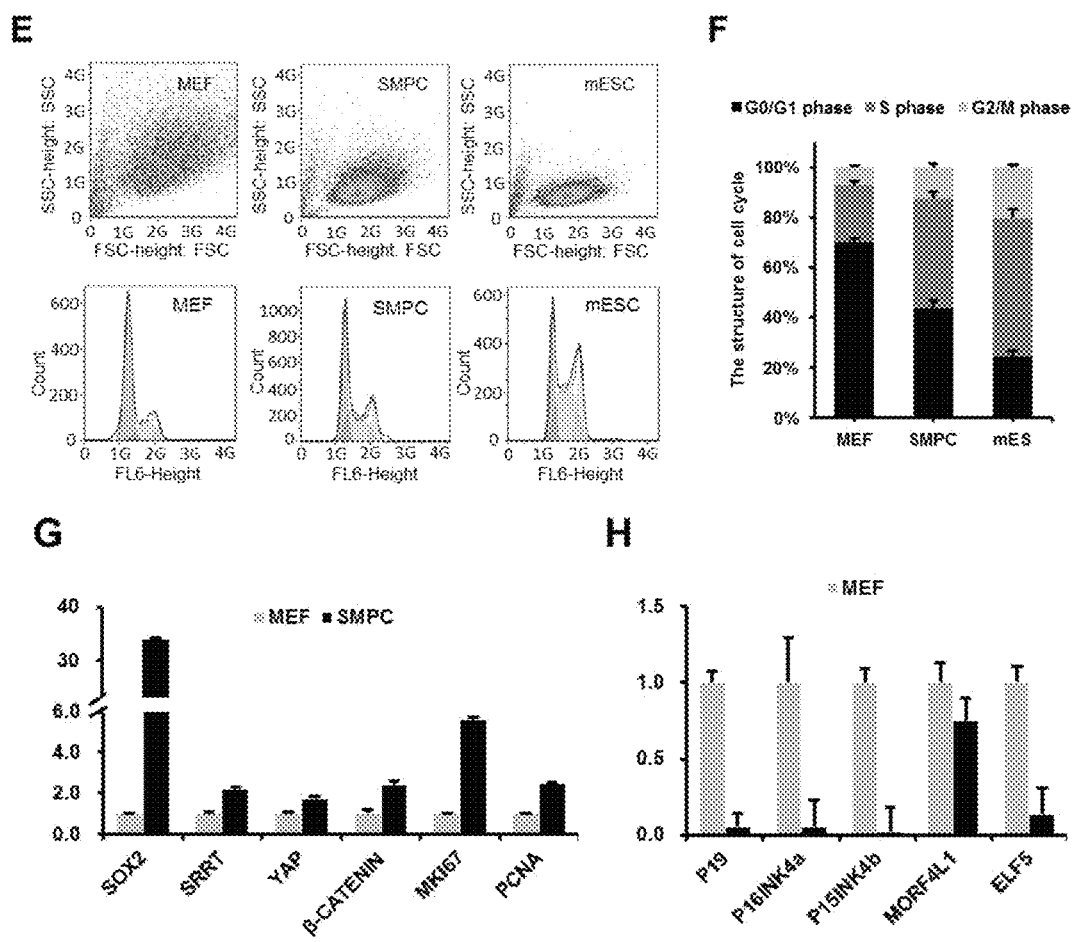

The fibroblasts treated as described above are added to an immortalization-inducing medium: (N2B27 medium: 1:1 mixture of DMEM/F12 (Gibco, 10565018) and Neurobasal (Gibco, 21103-049), added with N2 additive (100×, Gibco, 17502084), B27 additive (50×, Gibco, 17504044), 2% bovine serum albumin (1000×, sigma, A8022), β-mercaptoethanol (1000×, Gibco, 21985023), GlutaMAX (200×, Gibco, 35050-061), 1 μg/ml insulin (Roche, 11376497001), double antibiotics); adding 10% KOSR (gibco, 12618013), 3 μM CHIR99021 (stemgent, 04-0004-10), 10 M A83-01 (stemgent, 04-0014), and 25 μM Myosin inhibitor (−)-Blebbistatin (MCE, HY-13441), or 25 μM (S)-(−)-Blebbistatin O-Benzoate (TRC, B208070), and identifying after 21-28 days of culture, the experimental procedure is shown in FIG. 3A. The cells obtained by immortalization-inducing medium containing (−)-Blebbistatin (MCE, HY-13441) or (S)-(−)-Blebbistatin O-Benzoate (TRC, B208070) are subjected to the following experiments to identify whether they are the immortalized cells (SMPCs).

The identification of immortalized cell SMPCs mainly includes the followings:

Staining the stem cell marker. The experimental method is as follows: firstly, the Stem Cell CDy1 Dye is diluted with PBS at a ratio of 1:40 to prepare a CDy1 dilution buffer, and then the CDy1 dilution buffer is diluted with the medium at a ratio of 1:100 to prepare a CDy1 staining solution. After removing the medium, the CDy1 staining solution is added to stain the cells for 1 hour in 37° C., $CO_2$ incubator, washing three times with PBS, and then adding the medium to fade the color for 3 hours in a 37° C., $CO_2$ incubator. Observing with a fluorescence microscope, the results are shown in FIG. 3B, in which Merge indicates an overlapping pattern. Untreated mouse fibroblasts are not stained by CDy1; cells treated with immortalization-inducing medium (we call them SMPCs) are stained by CDy1, indicating that they obtained "stemness".

Plotting the cell growth curve. The experimental method is as follows: the immortalized cells (SMPCs) (second and fourth generation mouse embryonic fibroblasts as a control) are uniformly inoculated into a 12-well plate, 2×10$^4$ cells per well. Counting with a hemocytometer every 24 hours, and plotting the cell growth curve, then the cell cycle is calculated. The results are shown in FIGS. 3C and 3D. SMPCs are able to proliferate rapidly with the same initial amount of cells, and at 24, 48, 72, and 96 hours, the amount of cells is significantly higher than that of the control ($P<0.001$). The calculated cell cycle shows that, the cell cycle period of SMPCs is 16 hours, and it is significantly shorter than that of the second and fourth generation mouse embryonic fibroblasts: 36 hours and 45 hours (P<0.001).

Composition analysis of the cell cycle. The experimental method is as follows: immortalized cells (mouse embryonic fibroblasts and mouse embryonic stem cells as a control) are digested with 0.25% trypsin, terminating with DMEM+10% FBS and centrifuging, then discarding the supernatant; after resuspending in medium, passing through 400 mesh cell sieve, then the cell cycle is analyzed by a MoFlo XDP high-speed multicolor flow cytometer. The results are shown in FIGS. 3E and 3F. The homogeneity of the immortalized SMPCs is enhanced, and similar to that of the mouse embryonic stem cells. Moreover, G0/G1 phase of the immortalized cell SMPCs is shorter than that of the mouse embryonic fibroblasts, while the S phase is increased and similar to that of the mouse embryonic stem cells.

Example 3: Detection of Proliferation and Senescence Genes

The experimental method is as follows: the immortalized cells (SMPCs) (mouse embryonic fibroblasts as a control) are collected. (a) Extracting RNA by kit method. An appropriate amount of TRIzol is added to the cell pellet for lysing the cells, adding ⅕ volume of chloroform, vortexing to mix well, and then standing on ice for 3 min, centrifuging at 10,000 g for 15 min at 4° C. The upper aqueous phase is transferred to a new centrifuge tube, adding an equal volume of 75% ethanol, then transferring to an adsorption column, centrifuging at 10,000 g for 15 seconds, discarding the liquid in the collection tube; after washing once with Wash Buffer I, 10 µL of DNase I+70 µL Buffer RDD is added to the adsorption membrane, incubating for 15 min at room temperature to digest the DNA, followed by washing once with 350 µL of Wash Buffer I, and washing once with 500 µL of Wash Buffer II, then eluting RNA with RNase-free water. The concentration is measured by ultraviolet/visible spectrophotometer. (b) Reverse transcription of RNA into cDNA. Random primers, dNTPs are added to 2 µg of RNA sample, heating at 65° C. for 5 min to eliminate the high level structure of RNA, followed by quenching on ice for 3 min to bind the RNA template to the random primer. Reverse transcriptase and RNase inhibitor are added, conducting reverse transcription at 42° C. for 1 h to obtain cDNA. (c) Real-time fluorescent quantitative PCR is performed to detect the proliferation- and senescence-associated genes.

The PCR reaction system is as follows: 7.5 µL of SYBR Green Real Time PCR Master Mix, 2 L of Plus solution, 0.5 µL of primers (upstream and downstream mixing primers), 0.5 µL of cDNA, and 4.5 µL of double distilled water. The PCR reaction procedure is as follows: Amplification curve: 95° C., 2 min, denaturing at 95° C. for 15 seconds, annealing at 62° C. for 15 seconds, extending at 72° C. for 45 seconds, and detecting fluorescence signal after the end of extension. Melting curve: denaturing at 95° C. for 1 min, annealing at 57° C. for 30 seconds, and slowly renaturing to 95° C. for 30 seconds. The experiment is performed on an Agilent MX3005P fluorescence real-time quantitative PCR instrument by using Actb as a reference gene, and the results are treated by the ΔΔCt method. The results are shown in FIG. 1G and FIG. 1H. The expression levels of proliferation-related genes: Sox2, Srrt, Yap, β-catenin, Mki67, and Pcna in immortalized cells (SMPCs) are higher than that in mouse embryonic fibroblasts, while the expression levels of aging-related genes: P19, P16ink4a, P15ink4b, Morf4l1, and Elf5 are lower than that in mouse embryonic fibroblasts.

Example 4: Isolation and In Vitro Amplification of Mouse Adult Primary Hepatocytes Alb-Cre mice are introduced from BRL Medicine, Cre recombinase is only expressed in mature hepatocytes expressing albumin; Rosa26/mTmG mice are introduced from Charles River, and a red and green fluorescence reporter system is incorporated into the Rosa26 locus of this kind of mouse; normally a tomato red fluorescent protein is expressed in the cells, while in the case of Cre recombination it is changed to express a green fluorescent protein (GFP). Alb-Cre adult mice are hybridizedwith Rosa26/mTmG mice to obtain offspring Alb-Cre×Rosa26/mTmG mice, and mature hepatocytes of the offspring are labeled green, and other tissue cells present the red fluorescent.

Figure 4A:
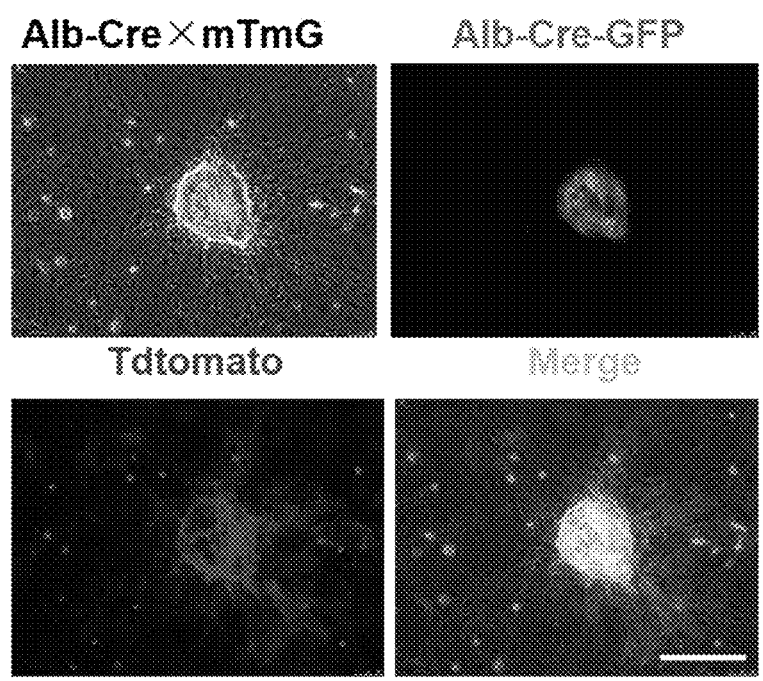
FIG. 4A shows that cells are resuspended in mouse hepatocyte medium (adding 5 μM Myosin II inhibitor (−)-Blebbistatin), and inoculated on a dish with fibronectin; one week later, green hepatocyte clusters with Alb expression are observed.

Alb-Cre×Rosa26/mTmG adult mice are sacrificed by cervical dislocation, taking out the hepatic lobes, cutting into small pieces, blowing and washing repeatedly with 100 volumes of pre-cooled PBS to remove the blood cells until the washing solution is not red; adding 3-5 volumes of collagenase IV (ThermoFisher, 17104019, preheated at 37° C.) to digest in incubator at 37° C. for 30-40 min, and blowing 2-3 times during the digestion, then centrifuging and removing the supernatant. Adding 3-5 volumes of trypsin (Gibco, 25300062) to digest in incubator at 37° C. for 20 min, then adding 2 volumes of 10% serum to terminate the digestion, centrifuging and taking out the supernatant; then the cells are suspended with mouse hepatocyte medium (adding 5 m of Myosin II inhibitor (−)-Blebbistatin), inoculating on a petri dish coated with fibronectin, and green hepatocyte clusters with Alb expression are observed one week later, as shown in FIG. 4A. The mouse hepatocyte medium comprises: DMEM/F12 (gibco, 10565018), adding N2 additive (100×, Gibco, 17502048), B27 additive (50×, Gibco, 17504044), 5% bovine serum albumin (1000×, Sigma, A8022), β-mercaptoethanol (1000×, Gibco, 21985023), GlutaMAX (200×, Gibco, 35050-061), non-essential amino acids (100×, Gibco, 11140-050), 1 µg/mL insulin (Roche, 11376497001), hepatocyte growth factor (10 ng/mL, R&D, 294-HG-025), transforming growth factor β inhibitor A83-01 (5 µm, stemgent, 04-0014), glycogen synthase kinase 3β inhibitor Chir99021 (6 µM, stemgent, 04-0004-10), macrophage stimulating protein 1 and 2 inhibitor XMU-MP-1 (2-5 µM, MCE, HY-100526) fibroblast growth factor 4 (10 ng/mL, R&D, 5846-f4-025), double antibiotics.

Figure 4B:
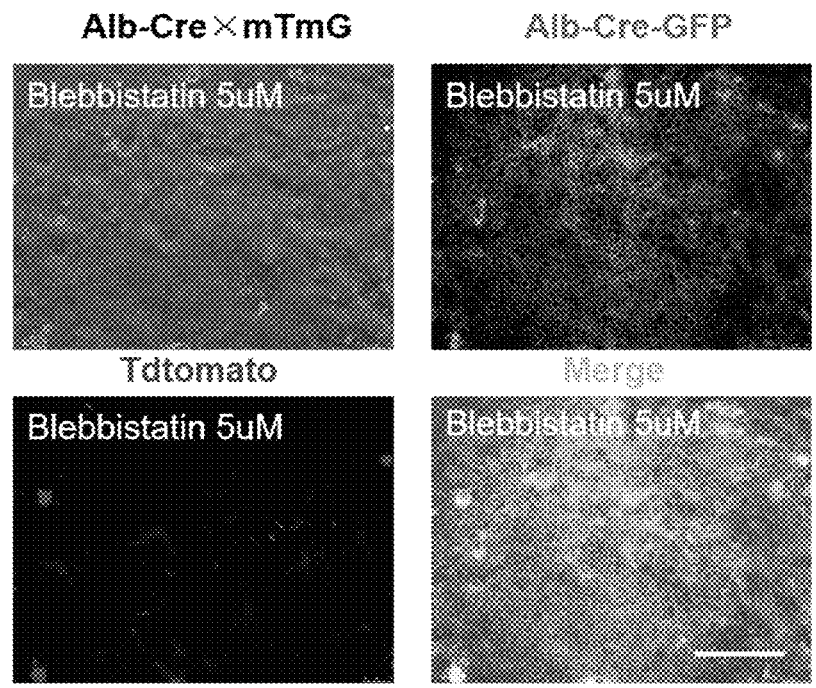
FIG. 4B shows the results of long-term amplification of AlB-GFP positive hepatocytes.
Figure 4B:
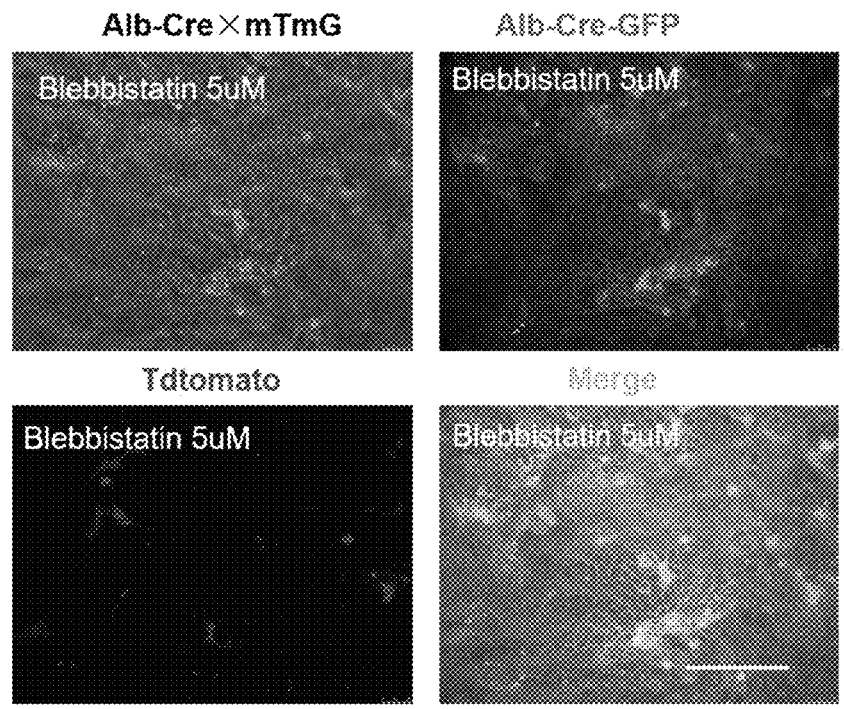
Figure 4B:
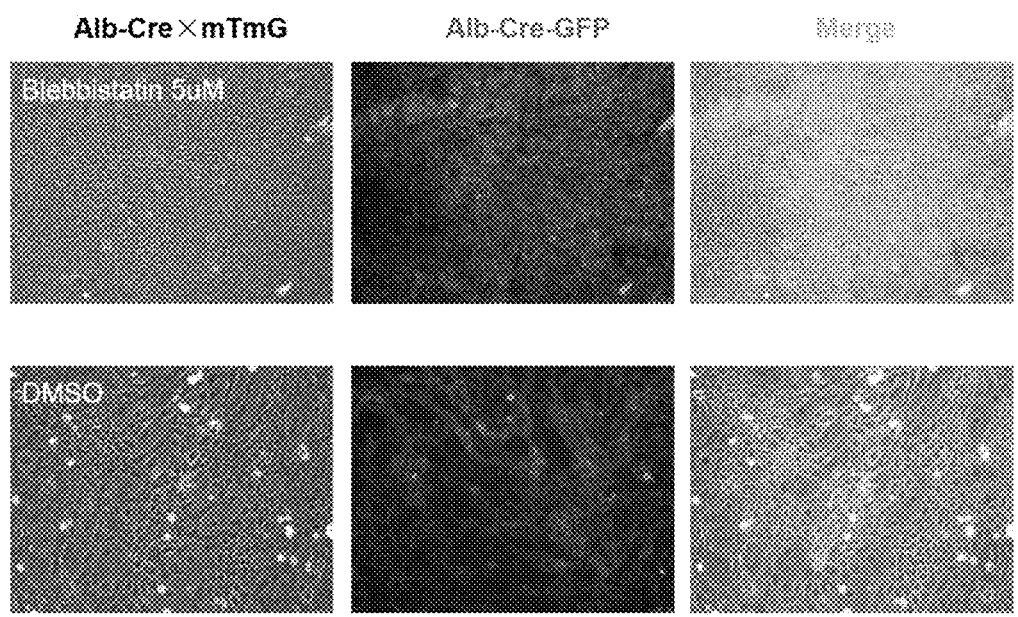

Without addition of Myosin II inhibitor (−)-Blebbistatin or (S)-(−)-Blebbistatin O-Benzoate, an equal volume of DMSO is added as a control, and the cells are respectively subcultured 3 times (P3), 5 times (P5), and seven times (P7). The results show that the addition of Myosin inhibitor (−)-Blebbistatin significantly promotes long-term amplification of AlB-GFP-positive hepatocytes (subculturing in vitro for at least 20 generations), as shown in FIG. 4B. In addition, the results also shows that the (−)-Blebbistatin derivative (S)-(−)-Blebbistatin O-Benzoate has a similar effect on hepatocyte passage amplification, and the treated hepatocytes can be passaged in vitro for more than 20 times.

Example 5: In Vitro Amplification of Human Embryonic Hepatocytes

1. Experimental Procedure (1) Coating the plate. The cell culture plate is coated with rat tail tendon collagen (Thermo scientific, A1048301, 3 mg/mL) at a concentration of 5 g/cm². Taking a 24-well plate as an example, the bottom area of each hole is 1.9 cm², and 9.5 ag is needed per well (about 3.2 μl); 3.2 μl of rat tail tendon collagen is dissolved in 500 μl of 20 mM glacial acetic acid, adding to the well to incubate in cell culture incubator at 37° C. for 1 h, and after aspirating and abandoning the solution, washing with PBS for 3 times.

(2) Resuscitation of human embryonic hepatocytes. Human embryonic hepatocytes are taken out from liquid nitrogen tanks (freezing date: Jan. 15, 2014; freezing medium: cell banker 2; the number of frozen cells: $2\times10^7$/tube), quickly placing in a 37° C. water bath, immediately after thawing the cells are sucked into a 15 mL centrifuge tube containing 5 mL of hepatocyte medium (control group), then centrifuging at 50 g, 4° C. for 5 min. The supernatant is discarded, then the cells are resuspended in 500 μl of hepatocyte medium with the number of $1.16\times10^6$ cells, and the cell resuscitation rate is 5.8%.

(3) Seeding the human embryonic hepatocytes. The cells are seeded at a density of $1\times10^5$/well in a 24-well plate, and 500 μl of hepatocyte medium (control group) are respectively added. The hepatocyte medium comprises: DMEM/F12 (gibco, 10565018), and adding N2 additive (100×, Gibco, 17502048), B27 additive (50×, Gibco, 17504044), 5% bovine serum albumin (1000×, sigma, A8022), β-mercaptoethanol (1000×, Gibco, 21985023), GlutaMAX (200×, Gibco, 35050-061), non-essential amino acids (100×, Gibco, 11140-050), 1 μg/mL insulin (Roche, 11376497001), fibroblast growth factor (10 ng/mL, R&D, 294-HG-025), transforming growth factor β inhibitor A83-01 (5 μM, stemgent, 04-0014), glycogen synthase kinase 3β inhibitor Chir99021 (6 μM, stemgent, 04-0004-10), macrophage stimulating protein 1 and 2 inhibitor XMU-MP-1 (2-5 μM, MCE, HY-100526), hepatocyte growth factor 4 (10 ng/mL, R&D, 5846-f4-025), double antibiotics. After hepatocyte medium containing 10 μM small molecule (−)-Blebbistatin, and hepatocyte medium containing 20 μM small molecule (−)-Blebbistatin hepatocyte medium are respectively seeded 24 h, for each group the digested cells from 3 wells are counted to calculate the cell attachment rate. After seeding for 72 h, for each group 3 wells of cells are digested and counted. The number of cells after seeding for 72 h is divided by the number of cells after seeding for 24 h to obtain the multiple of cell number change. A portion of the cells per well (⅖ of the cells counted) are taken for RNA extraction to detect the expression of human hepatocyte-associated genes.

(4) The first passage of human embryonic hepatocytes. The cells are inoculated into a 24-well plate coated with rat tail tendon collagen (as described above) at a density of ⅗ of the number of cells in the 72-hour primary culture; 3 duplicate wells per group. After 72 hours of cell culture, the cells are digested to count. The number of cells is divided by the number of cells at the time of inoculation to obtain the multiple of the first passage amplification. A portion of the cells per well (⅖ of the cells counted) are taken for RNA extraction to detect the expression of human hepatocyte-associated genes.

(5) The second passage of human embryonic hepatocytes. The cells are inoculated into a 24-well plate coated with rat tail tendon collagen (as described above) at a density of ⅗ of the number of cells in the 72-hour first subculture. Since most of the cells died after 72 hours of the first subculture in the control group, only a small number of cells are remained, and all of the remained cells are inoculated. The medium is changed every 2 days, and after continuing to culture for 144 h (6 days), the cells are digested and counted. The number of cells at this time is divided by the number of cells at the time of inoculation to obtain the multiple of the second passage amplification. Cell culture supernatants from each well are taken to detect the concentration of human albumin, and a portion of the cells (⅖ of the cells counted) are taken for RNA extraction to detect the expression of human hepatocyte-associated genes.

2. Results

Figure 5A:
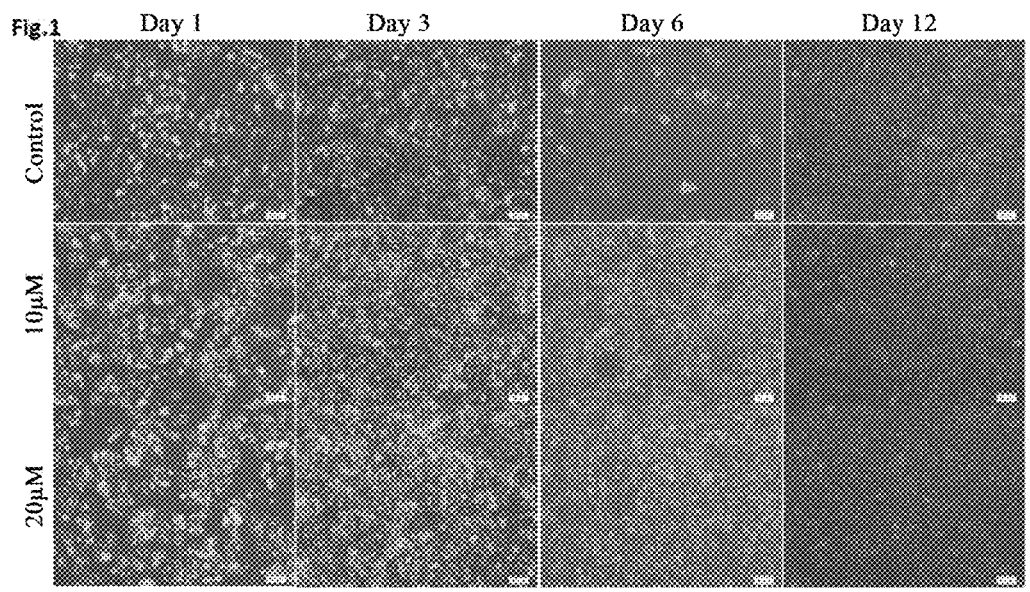
FIGS. 5A and 5B show the results of amplification after 12 days of subculturing (3 generations in total).
Figure 5B:
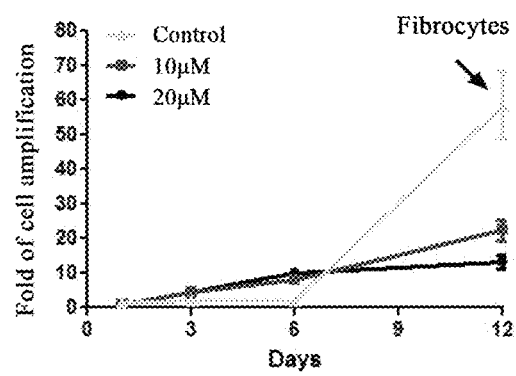
Figure 5C:
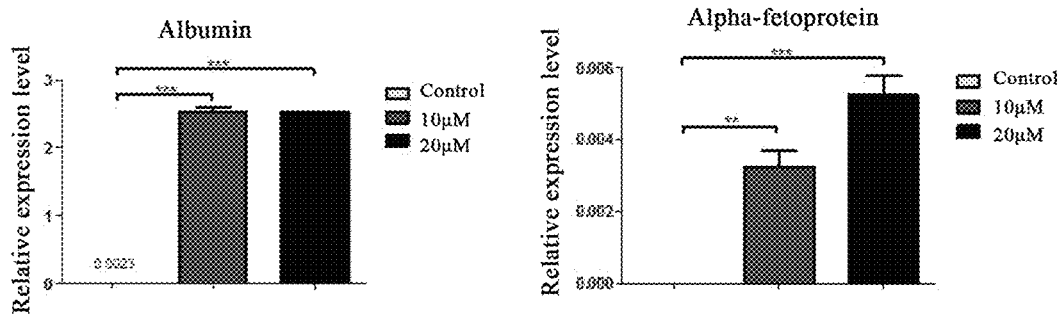
FIG. 5C shows the gene expression results of albumin and alpha-fetoprotein after 12 days of subculturing (3 generations in total).

After three and a half years of liquid nitrogen cryopreservation of human embryonic hepatocytes, the resuscitation rate of the cells is about 5.8%. As shown in FIG. 5A and FIG. 5B, after subculturing in a small molecule medium (3 generations in total) for 12 days, the cells may be amplified by about 22.1 times (SD=4.2) in 10 μM small molecule medium, and may be amplified by about 13.0 times (SD=3.39) in 20 μM small molecule medium. At this time, the cell morphology is still the typical hepatocyte morphology, showing an irregular polygon. However, after subculturing in the medium of control group, since most of the cells died after the first subculture, and the remaining small part of cells are cultured and amplified up to 58.3 times until 12 days later (SD=13.9), but at this time, the cells are in the form of typical hepatocytes, being slender and flat. As shown in FIG. 5C, real-time quantitative PCR is used to detect human hepatocyte-specific gene albumin and alpha-fetoprotein. The results show that the human hepatocyte-specific genes are still expressed in human hepatocytes after subculturing for 12 days in 10 μM and 20 μM small molecule media; while in the cells obtained after subculturing for 12 days control medium, very low albumin expression and no alpha-fetoprotein gene expression is detected, indicating that the cells at this time are not hepatocytes, and the results are consistent with those in FIG. 5A and FIG. 5C.

Example 6: Small Molecule Amplification of Adult Hepatocytes

1. Experimental Procedure (1) The method for coating the plate is as described above.

(2) Resuscitation and culture of adult hepatocytes. Adult hepatocytes (M00995-P Male human, Bioreclamation IVT) are taken out from a liquid nitrogen tank, then quickly placing in a 37° C. water bath, after thawing the cells are added to 5 mL of 37° C. pre-heated hepatocyte inoculation medium (InVitroGRO CP Medium), after counting the cells are inoculated in a 24-well plate at the density of $9\times10^4$/well, 2-4 h after hepatocyte adherence, aspirating and abandoning the hepatocyte inoculation medium, and respectively adding hepatocyte culture control medium, 10 μm small molecule medium, and 20 μm small molecule medium. The media are changed every 2 days. The number of cells is estimated from the photograph on day 2. After 4 days, the cells of the 20 μm small molecule medium group are changed to culture in 10 μm small molecule medium. The cells are counted after co-culturing for 6 days. A portion of the cells are taken for RNA extraction to detect the expression of human hepatocyte-specific genes.

(3) Passage of adult hepatocytes. $4.7\times10^4$ of the hepatocytes cultured in the above-mentioned control group, and $8\times10^4$ of the hepatocytes cultured 10 μm small-molecule medium are respectively re-inoculated into the 24-well plates coated with rat tail tendon collagen, and the media are changed every two days. After 6 days, photos are taken to record cell growth.

(4) 10CYP1A2 adult hepatocytes amplified in 10 μm small medium. 3×10⁵ hepatocytes are induced and inoculated in a 24-well plate coated with rat tail tendon collagen, after culturing in a 10 μm small molecule medium for 24 h, then replacing the medium with a 10 μm small molecule medium with 50 μm omeprazole, the control group is a 10 μm small molecule medium containing DMSO, and 48 hours later the cells are collected to detect the expression of the CYP1A2 gene.

2. Results

Figure 6A:
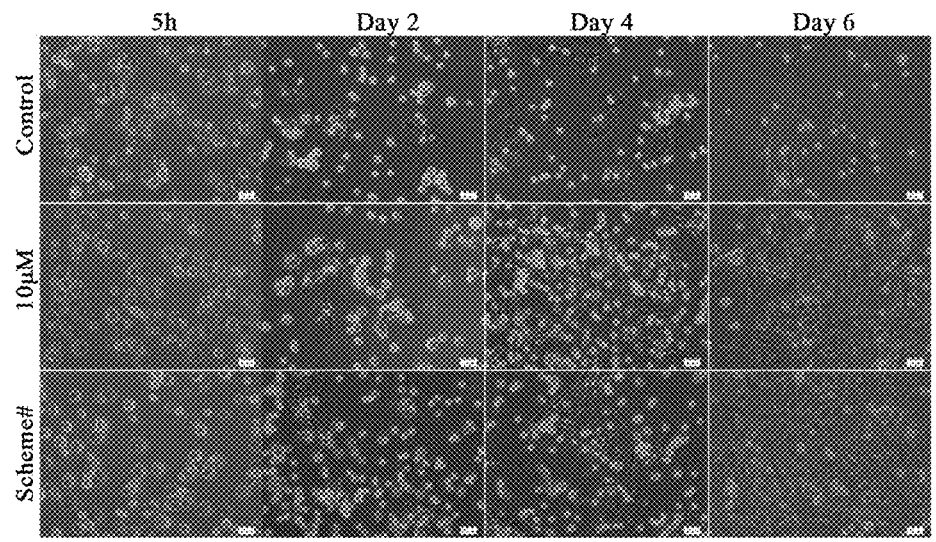
FIG. 6A shows that after two days of continuous cultivation, cell colonies of the small molecule group are further amplified, while the control group shows no significant change.
Figure 6B:
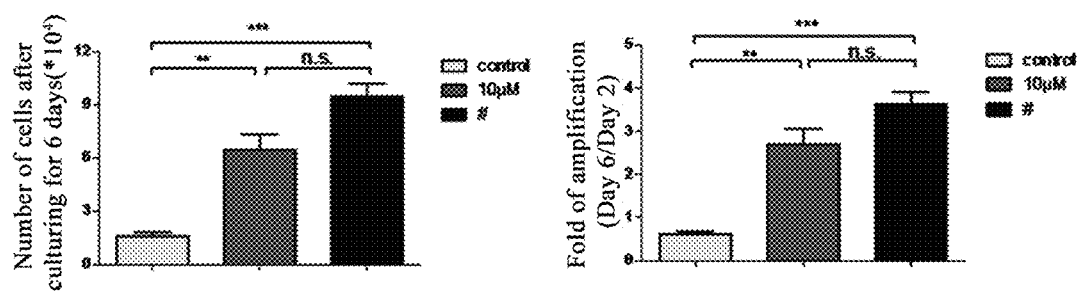
FIG. 6B shows the number of cells of the small molecule group and the control group after 6 days of cultivation.
Figure 6C:
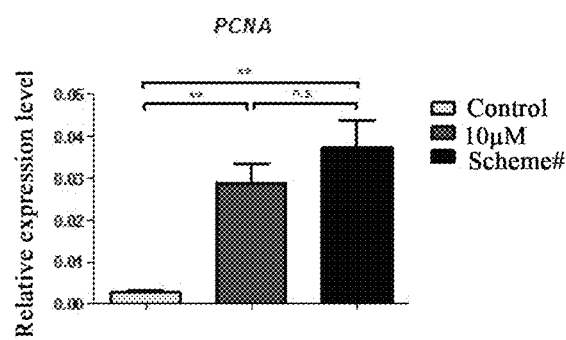
FIG. 6C shows the expression results of the proliferating cell nuclear antigen (PCNA) gene in the small molecule group and the control group.
Figure 6D:
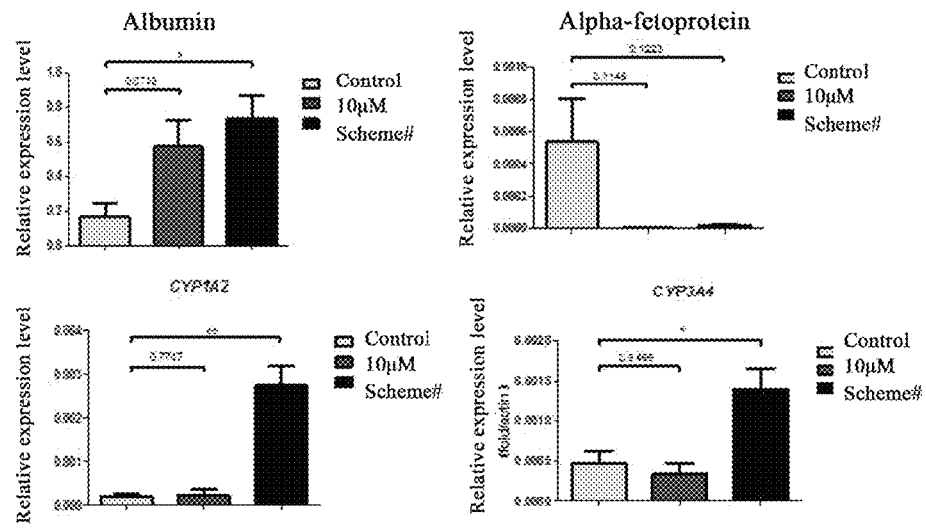
FIG. 6D shows the expression results of human hepatocyte specific genes albumin (albumin), alpha fetoprotein (AFP), CYP1A2 and CYP3A4 in adult hepatocytes amplified with small molecules.
Figure 6E:
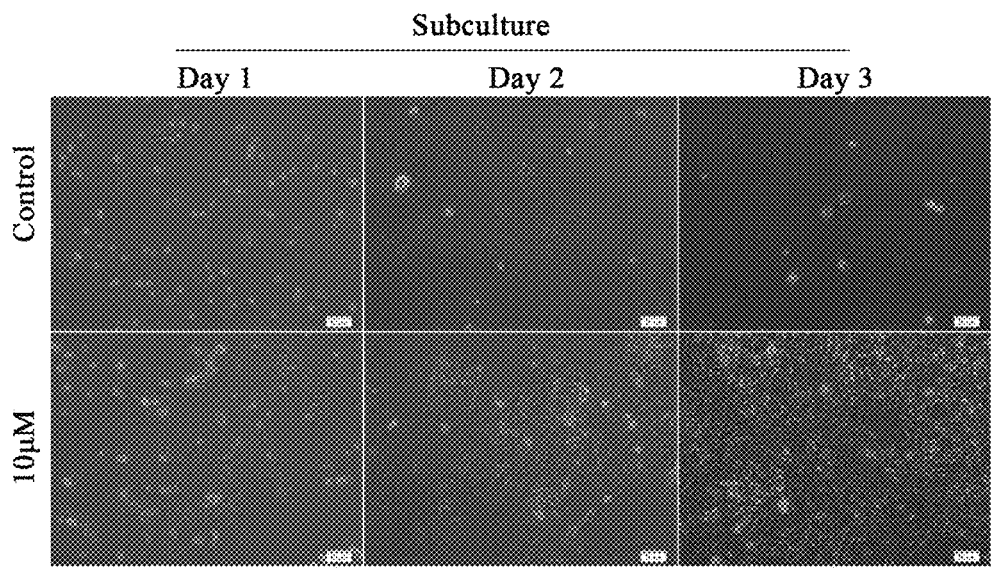
FIG. 6E shows the results of human hepatocytes subcultured with 10 m small molecule medium and control medium respectively.
Figure 6F:
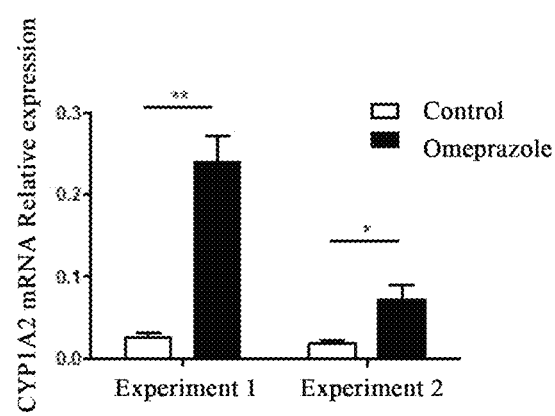
FIG. 6F shows the expression results of CYP1A2 gene in subcultured adult hepatocytes after inducing with omeprazole.

Five hours after inoculation, the attachment rates of adult hepatocytes are similar, and 2 days later, the cells of the control group, the 10 μm small molecule group, and the 20 μm small molecule group die in large numbers; taking photos and estimating the number of living cells attached (2.53×10⁴, SD=0.09). On day 4, the small molecule group begins to show amplification colonies, while the control group does not significantly amplify. At this time, the 20 μm medium group is replaced with a 10 μm small molecule medium (named protocol #, i.e., culturing at "20 m" for 4 days, and culturing at "10 m" for 2 days). After two days of continuously culturing, the cell colonies of the small molecule group are further amplified, while the control group shows no significant change (FIG. 6A). After 6 days of culturing, the number of cells respectively is 1.59×10⁴ (SD=0.28) in the control group, 6.47×10⁴ (SD=1.24) in the 10 μm group, and 9.47×10⁴ (SD=0.98) in the #group (FIG. 6B). The cell number on day 6 is divided by the cell number on day 2 to obtain the multiple of amplification, and the results show that the small molecules have a significant amplification effect on adult hepatocytes (FIGS. 6A and 6B). The expression of the proliferating cell nuclear antigen (PCNA) gene is significantly higher in the small molecule group than that in the control group, further demonstrating that the small molecules have an effect on cell proliferation (FIG. 6C). Adult hepatocytes amplified with small molecules still express human hepatocyte specific gene albumin, alpha fetoprotein (AFP), CYP1A2, CYP3A4 (FIG. 6D). The 10 μm small molecule medium can make human hepatocytes subculture, while the control medium cannot make the adult hepatocytes subculture (FIG. 6E). After induction with omeprazole, the expression of CYP1A2 gene in the subcultured adult hepatocytes can be increased, suggesting that small molecule-amplified hepatocytes are still functional (FIG. 6F).

The foregoing merely illustrates the principle of the present invention. It should be understood that the scope of the present invention is not intended to be limited to the exemplary aspects described herein, but should include all the currently known and future developed equivalents. In addition, it should be noted that a number of improvements and modifications may be made without departing from the spirit of the present invention, and such modifications and modifications are also considered to be within the scope of the present invention.

The invention claimed is:

1. A method for inducing in vitro amplification of hepatocytes, comprising the steps of culturing hepatocytes in a medium, adding a Myosin inhibitor to the medium, and continuously culturing the cells to induce in vitro amplification of hepatocytes, wherein the medium comprises DMEM/F12, N2 additive, 5% bovine serum albumin, β-mercaptoethanol, L-alanyl-L-glutamine dipeptide, non-essential amino acids, insulin, hepatocyte growth factor, A83-01, Chir99021, XMU-MP-1, fibroblast growth factor 4 and double antibiotics.

2. The method according to claim 1, wherein the Myosin inhibitor is (−)-Blebbistatin, or (−)-Blebbistatin O-Benzoate.

3. A medium for inducing in vitro amplification of hepatocytes, comprising: (−)-Blebbistatin or (−)-Blebbistatin O-Benzoate, and hepatocyte medium, wherein the hepatocyte medium comprises DMEM/F12, N2 additive, 5% bovine serum albumin, β-mercaptoethanol, L-alanyl-L-glutamine dipeptide, non-essential amino acids, insulin, hepatocyte growth factor, A83-01, Chir99021, XMU-MP-1, fibroblast growth factor 4 and double antibiotics.

* * * * *